United States Patent
Pekar et al.

(10) Patent No.: US 10,672,202 B2
(45) Date of Patent: Jun. 2, 2020

(54) CONFIGURABLE INFERENTIAL SENSOR FOR VEHICLE CONTROL SYSTEMS

(71) Applicant: GARRETT TRANSPORATION I INC, Torrance, CA (US)

(72) Inventors: Jaroslav Pekar, Pacov (CZ); Ondrej Santin, Svijany (CZ)

(73) Assignee: GARRETT TRAN SPORATION I INC., Torrance, CA (US)

( * ) Notice: Subject to any disclaimer, the term of this patent is extended or adjusted under 35 U.S.C. 154(b) by 301 days.

(21) Appl. No.: 14/929,484

(22) Filed: Nov. 2, 2015

(65) Prior Publication Data

US 2016/0125672 A1    May 5, 2016

(30) Foreign Application Priority Data

Nov. 4, 2014  (EP) ..................... 14191767

(51) Int. Cl.
*G07C 5/08* (2006.01)
*G07C 5/02* (2006.01)
(Continued)

(52) U.S. Cl.
CPC .............. *G07C 5/08* (2013.01); *F01N 11/005* (2013.01); *F01N 11/007* (2013.01);
(Continued)

(58) Field of Classification Search
CPC ....................................................... G07C 5/08
See application file for complete search history.

(56) References Cited

U.S. PATENT DOCUMENTS

| | | | |
|---|---|---|---|
| 6,347,512 B1 * | 2/2002 | Kolmanovsky | F02D 41/0275 60/274 |
| 8,700,546 B2 | 4/2014 | Germann et al. | |

(Continued)

FOREIGN PATENT DOCUMENTS

| | | |
|---|---|---|
| EP | 1367248 | 3/2003 |
| FR | 2783940 | 3/2000 |

OTHER PUBLICATIONS

Extended European Search Report for EP Application No. 14191767.4-1807, dated Apr. 17, 2015.
An Office Action for EP Application No. 14191767.4, dated Oct. 27, 2017.

*Primary Examiner* — Raymond L Nimox
(74) *Attorney, Agent, or Firm* — Seager, Tufte & Wickhem, LLP

(57) ABSTRACT

A system that provides an estimation of quantities, which are not necessarily directly measurable in a subsystem. The estimates of these quantities may be inferred from other variables. This approach may be referred to as inferential sensing. Physical sensors may be replaced with models or virtual sensors, also known as inferential sensors. The present approach may be a framework for designing inferential sensors in automotive subsystems. The framework may incorporate preparing a model for an observed subsystem, populating a real-time template with data, and running an inferential sensor periodically together with a model in real-time to obtain estimated variables. Once implemented, the framework may be reused for virtually any automotive subsystem without needing significant software code changes.

15 Claims, 7 Drawing Sheets

(51) Int. Cl.
    *G01N 33/00*     (2006.01)
    *F01N 11/00*     (2006.01)
    *F02M 35/10*     (2006.01)
    *G05B 23/02*     (2006.01)
    *G05B 17/02*     (2006.01)
    *G05B 13/04*     (2006.01)

(52) U.S. Cl.
CPC ..... *F02M 35/1038* (2013.01); *G01N 33/0037* (2013.01); *G05B 13/04* (2013.01); *G05B 17/02* (2013.01); *G05B 23/0221* (2013.01); *G07C 5/02* (2013.01); *F01N 2550/02* (2013.01); *Y02A 50/245* (2018.01)

(56) References Cited

U.S. PATENT DOCUMENTS

| | | | |
|---|---|---|---|
| 9,115,635 B2 | 8/2015 | Abou-Nasr et al. | |
| 2003/0216855 A1* | 11/2003 | Liang | F01N 3/208 701/114 |
| 2004/0024565 A1* | 2/2004 | Yu | B60G 17/0182 702/151 |
| 2008/0229728 A1* | 9/2008 | Stewart | F01N 3/208 60/274 |
| 2009/0133384 A1* | 5/2009 | Devarakonda | F01N 3/106 60/276 |
| 2011/0214650 A1* | 9/2011 | Wang | F02D 41/00 123/703 |
| 2013/0159225 A1* | 6/2013 | Germann | G01D 18/008 706/12 |
| 2013/0173028 A1* | 7/2013 | Felty | G05B 13/02 700/79 |

\* cited by examiner

Fig. 3

$$\dot{x}(t) = f(x(t), u(t), \theta(t)) + v(t)$$
$$y(t) = g(x(t), u(t), \theta(t)) + e(t)$$ ⤳ 61

Fig. 4

$$\frac{\partial f(.)}{\partial x(t)}, \frac{\partial g(.)}{\partial x(t)}$$ ⤳ 62

$$y_{j+1} = y_j - \left(h\frac{\partial f(y_j, u_k)}{\partial y_j} - I\right)^{-1} (hf(y_j, u_k) + x_k - y_j), \ y_0 = x_k, x_{k+1} \approx y_j$$

$$J_{k+1|k} = 0.5 I - h\frac{\partial f(x_{k+1|k}, u_k)}{\partial x_{k+1|k}}$$

$$0 = J_{k+1|k} P_{k+1|k} + P_{k+1|k} J_{k+1|k}^T + P_{k|k} + hQ$$

CONFIGURABLE INFERENTIAL SENSOR FOR VEHICLE CONTROL SYSTEMS

BACKGROUND

The present disclosure pertains to measurements of quantities of systems and particularly to measurements of quantities that are not necessarily easily measurable.

SUMMARY

The disclosure reveals a system that may provide an estimation of quantities that are either not directly or not easily measurable in a subsystem. The estimates of these quantities may be inferred from other variables. This approach may be referred to as inferential sensing. Physical sensors may be replaced with models or virtual sensors, also known as inferential sensors. The present approach may be a framework for designing inferential sensors for automotive subsystems. The framework may incorporate preparing a model for an observed subsystem, populating a real-time template with data, and running an inferential sensor periodically together with a model in real-time to obtain estimated variables. Once implemented, the framework may be reused for virtually any automotive subsystem without needing significant software code changes.

BRIEF DESCRIPTION OF THE DRAWING

FIG. 3 shows a set of nonlinear ordinary differential equations that may be used in a nonlinear model for the inferential sensor;

FIG. 4 shows an analytical first derivative of ordinary differential equations;

FIG. 5 shows an Euler method;

FIG. 6 shows a backward Euler or implicit method;

FIG. 8 shows an implicit Euler method based on a Newton-Raphson or Levenberg-Marquardt approach;

FIG. 9 shows equations for an implicit time step update for the algorithmic framework;

DESCRIPTION

Figure 1:
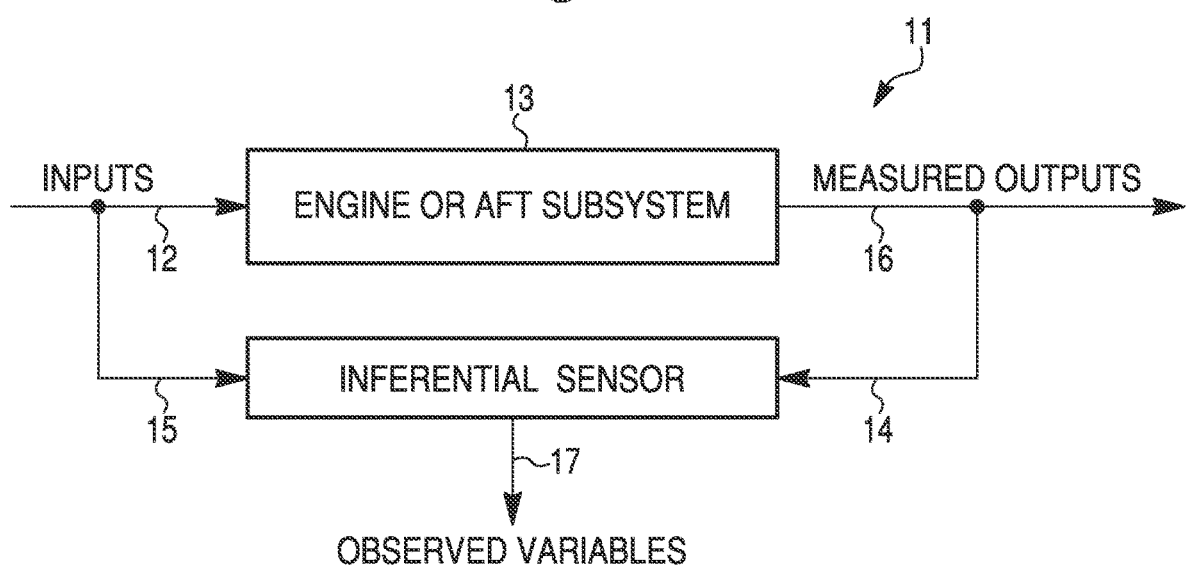
FIG. 1 is a diagram of an application of an inferential sensor for an automotive control system.

The present system and approach may incorporate one or more processors, computers, controllers, user interfaces, wireless and/or wire connections, and/or the like, in an implementation described and/or shown herein.

This description may provide one or more illustrative and specific examples or ways of implementing the present system and approach. There may be numerous other examples or ways of implementing the system and approach.

The complexity of modern internal combustion engines appears to be rapidly growing as a response to tighter emission requirements prescribed by legislation. Each new restriction may often lead to adjusting or adding a new subsystem or technology. Virtually all additional subsystems may then need a new control system to achieve the desired performance and ensure that tailpipe emission restrictions will be satisfied over the engine lifetime.

To monitor and control new subsystems, it may often be necessary to introduce one or several additional sensors and actuators. New sensors and actuators appear to be increasing not only in complexity but also in a final price of the product. The aftertreatment line may be an example of such a subsystem. The SCR (selective catalytic reduction) may be a device used to remove NOx from the exhaust gas by introducing ammonia (NH3) which is decomposed from injected urea. Prescribed legal limits have to be satisfied for both NOx and NH3 emissions and therefore efficient and precise control systems for urea injector may be needed. A feedback control system should to know the internal state of a catalyst, including namely ammonia coverage which drives the NOx conversion efficiency. This quantity may have to be inferred from other variables since direct measurement is not apparent. Other examples of variables which may improve the response of an engine when introducing them to the control system incorporate an engine out NOx concentration, intake and exhaust oxygen concentration, in cylinder oxygen fraction, and other factors.

It may not be possible to introduce these mentioned sensors due to cost, reliability and maintenance reasons. Further, there appears to be a pressure to replace as many physical sensors from engine and coupled subsystems as possible by using models and virtual sensors, where the main reason for such replacement may be the cost of sensors, their reliability and related on board diagnostics (OBD).

The physical sensors may be replaced by models or virtual sensors, known also as inferential sensors when some advanced methods for observing the quantities are used. Replacement of a physical sensor may often be a difficult task requiring much labor and testing at significant expense. An approach may be to develop a concrete virtual sensor for a concrete quantity. When there is a need for observing a new physical quantity, it may be necessary to repeat the development work from beginning if a nonsystematic approach is used.

The present approach may be a framework for designing inferential sensors for use in automotive subsystems in a very systematic way. Further, mathematical techniques used in the described framework may ensure numerical robustness and be fast enough for implementation on embedded platforms for real-time control systems, known as an ECU (engine control unit).

The present approach may allow one to design, configure and calibrate various inferential sensors for internal combustion engines and aftertreatment systems in a systematic way, through: 1) preparing a model for the observed subsystem; 2) populating the real-time template with data, known as a calibration data set; and 3) running the inferential sensor periodically together with the model in the real-time to get the needed estimated variables.

Once implemented, the framework may be reused for virtually any subsystem on an engine without needing significant or onerous code changes. For example, the framework may be used for estimating non-measurable physical quantities in an aftertreatment line (e.g., ammonia storage, NO/NO2 ratio, and so forth). Further, there may be a potential for vehicle, engine and aftertreatment systems physical sensors' replacements or elimination (e.g., engine out NOx physical sensor, intake manifold oxygen sensor, tailpipe out NH3 physical sensor, SCR mid-brick NH3 physical sensor, and so on). The present inferential sensor may also be configured to estimate cross-sensitivity of NOx sensors to NH3, SCR inlet NO/NO2 ratio, and more. Such an approach may significantly reduce the development time and thus reduce the overall cost of a control system design while improving performance of the system.

The present approach may strictly separate the off-line and real-time parts which can be enabled by utilizing advanced observer methods. The approach may allow implementing and re-using the real-time part for a future inferential sensor of an engine or aftertreatment subsystem without making significant or onerous code changes.

The present inferential sensor may be implemented and applied as a computer program which might be executed on an engine control unit (ECU) or rapid prototyping system. The inferential sensor may have off-line and on-line (or real-time) parts. The parts may be implemented as in the following.

The off-line part may incorporate: 1) A manual or automatic preparation of the model of a subsystem that is a subject of inferential sensor in a suitable form for real time execution (e.g., a C language file), and the model is described by a set of ordinary differential equations (ODE); and 2) a manual or automatic preparation of the parameter data set for the model which may be stored in an automatically generated file (e.g., a C language file or header file).

The on-line part may be implemented by using an extended Kalman filter with certain components that incorporate: 1) an implicit fixed step solver (e.g., an implicit Euler method) to update the system model state, and the solver may use an iterative Newton-Raphson, Gauss-Newton or Levenberg-Marquardt algorithm; 2) A covariance matrix of the system state estimate may be stored and updated based on measured data in a factorized form, e.g., a Cholesky factorization or $LDL^T$ decomposition, and the factorized form may improve numerical properties of the method; and 3) A time update of the covariance matrix of the system state estimate may be done in an implicit form by solving a continuous Lyapunov equation in a Cholesky or $LDL^T$ factorized form, e.g., by using Hammarling's algorithm or its modifications.

Some observations may be noted. The present approach may be referred to as an implicit extended Kalman filter. The off-line part may need to be repeated for each new subsystem that is a subject of inferential sensor, i.e., both steps 1 and 2. Just step 2 of the off-line part may be needed if the model of the subsystem already exists and there is a need for new application of that inferential sensor. The online part may have to be implemented just once and thus it will not necessarily have to change for any new subsystem. This systematic approach may save much development work when designing a new inferential sensor. The present approach may be used for various engine subsystems. A few examples may encompass an estimation of ammonia storage in an SCR catalyst, an estimation of an SCR inlet NO/NO2 ratio, an estimation of cross-sensitivity parameters of a NOx sensor, an estimation of intake manifold/incylinder/exhaust manifold oxygen content or pressure, an estimation of engine out NOx, turbocharger speed, and so forth.

FIG. 1 is a diagram of an application of an inferential sensor system 11 for an automotive subsystem. Port 12 and 15 may be for conveying inputs to an engine or AFT subsystem 13, and an inferential sensor 14, respectively. Measured outputs from engine or AFT subsystem 13 may be provided at a port 16. The outputs from port 16 may go to an input port 14 of inferential sensor 14. Observed variables may be output at port 17.

Figure 2:
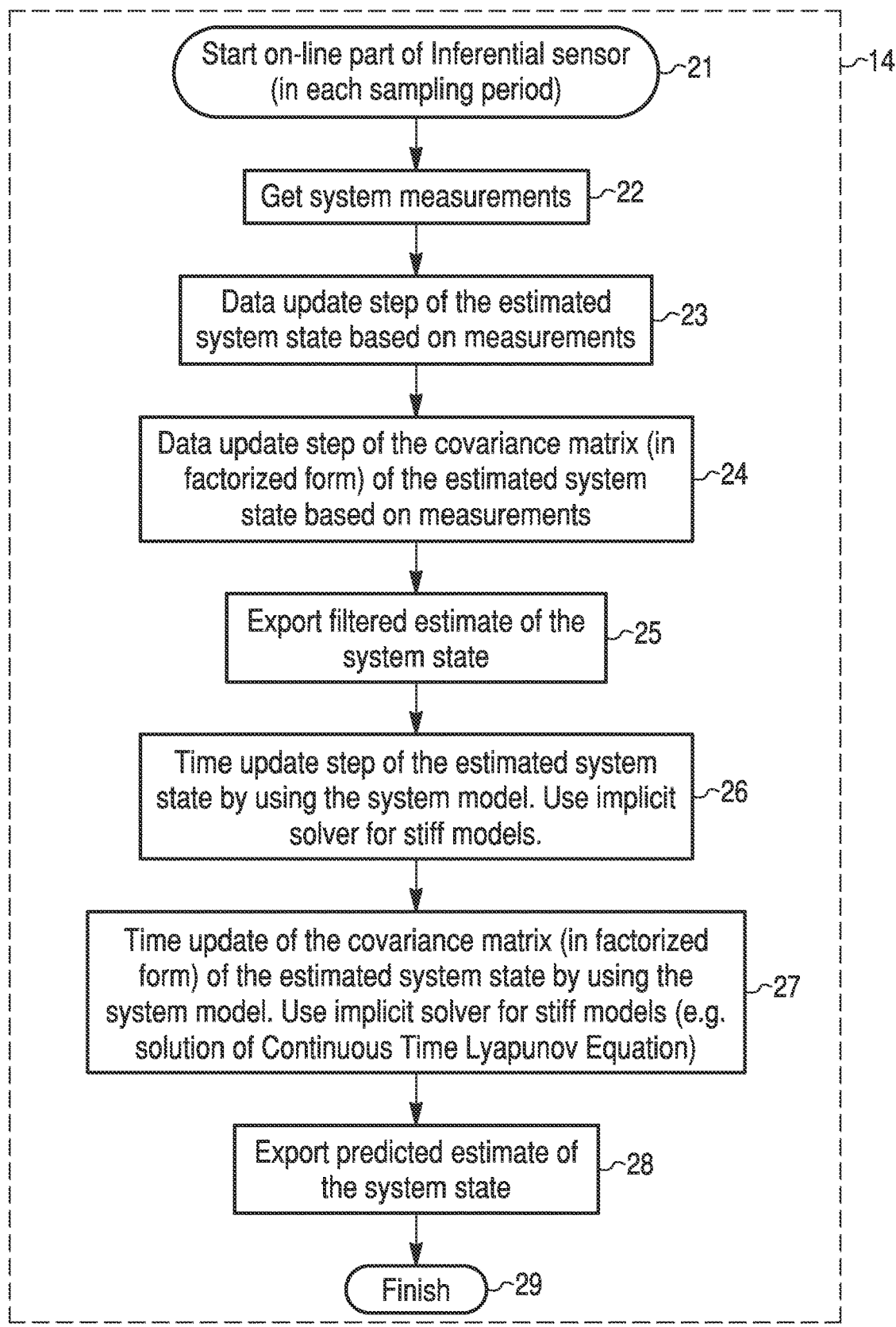
FIG. 2 is a flow diagram of the inferential sensor.

FIG. 2 is a flow diagram of inferential sensor 14. There may be a start-on-line part of sensor 14, for each sampling period, at symbol 21. System measurements may be obtained at a symbol 22. There may be a data update step of the estimated system state based on measurements at a symbol 23.

There may be a data update step of a covariance matrix (in factorized form) of the estimated system state based on measurements at symbol 24. A filtered estimate of the system state may be exported at a symbol 25. A time update step of the estimated system state by using the system model may be at symbol 26. An implicit solver may used for stiff models.

A time update of the covariance matrix (in factorized form) of the estimated system state may be effected by using the system model at symbol 27. An implicit solver may be used for stiff models (e.g., a solution of a continuous Lyapunov equation). A predicted estimate of the system state may be exported at symbol 28. The workflow may end at symbol 29.

An ammonia coverage inferential sensor may be noted. Components of an algorithmic framework and application to ammonia storage may be checked. The inferential sensor may be used to estimate unmeasured variables by using available measurement signals. The sensor may be executable on an engine control unit with single precision. The main parts of the sensor may incorporate a non-linear model of the system, a numerical observer for the non-linear model, and a state observer to update unmeasured variables.

The nonlinear model of the system may have a set of possibly stiff nonlinear ordinary differential equations such as equations 61 in FIG. 3. An analytical first derivative 62 in FIG. 4 may be of a great advantage.

The numerical solver for the nonlinear model may be fast and numerically robust. A simple option may be an Euler method 63 in FIG. 5. Euler method 63 may be numerically unstable, namely for stiff systems, and thus is not necessarily used for real practical issues. Another simple option may be a backward Euler method, which may have great stability for stiff equations. The backward Euler method 64 in FIG. 6 may be a basic approach for practical applications. Method 64 may be used to solve a set of nonlinear equations.

Figure 7:
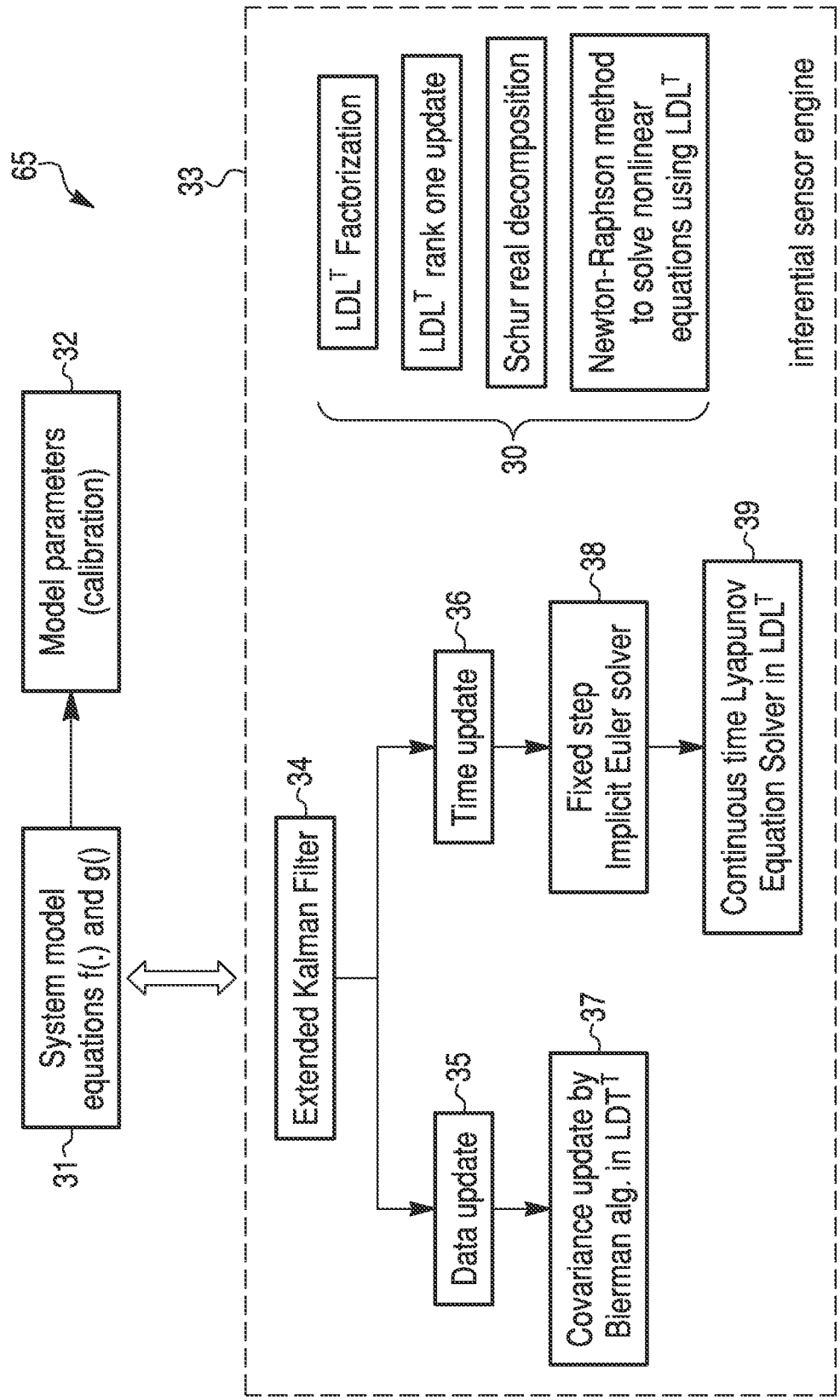
FIG. 7 is a diagram for an algorithmic framework of an inferential sensor.

FIG. 7 is a diagram for an algorithmic framework 65 of an inferential sensor. A system model 31 may have equations f(.) and g( ). Model 31 may provide model parameters 32 for calibration.

System model 31 may interact with an inferential sensor engine 33. Engine 33 may incorporate an extended Kalman filter 34 which may provide a data update 35 and a time update 36. Data update 35 may involve a covariance update 37 by a Bierman algorithm in $LDL^T$. Time update 36 may involve a fixed step implicit Euler solver 38 which in turn may involve a continuous Lyapunov equation solver 39 in $LDL^T$.

A group 30 of additional items for engine 33 may incorporate $LDL^T$ factorization, an $LDL^T$ rank one update, Schur real decomposition, and a Newton-Raphson method to solve nonlinear equation using $LDL^T$. Other items may be incorporated.

A numerical solver for ordinary differential equations may incorporate, for instance, backward or implicit Euler method 64 of FIG. 6, based on a Newton-Raphson or Levenberg-Marquardt method, may be shown as an equation 66 FIG. 8. A solution may need just one to three iterations if a good starting point is provided. A previous state may be a very good estimate. The solution may be very fast especially if a Jacobian can be derived analytically.

Extended Kalman filter 34 may involve possible numerical issues with stability during a time update step 36 of FIG.

7 in view of equations 61 in FIG. 3. An implicit time update step 36 may involve equations 67 in FIG. 9. Data update step 35 of extended Kalman filter 34 may be implemented with a covariance update by a Bierman algorithm in an $LDL^T$ factorization to get a numerical robustness.

Figure 10:
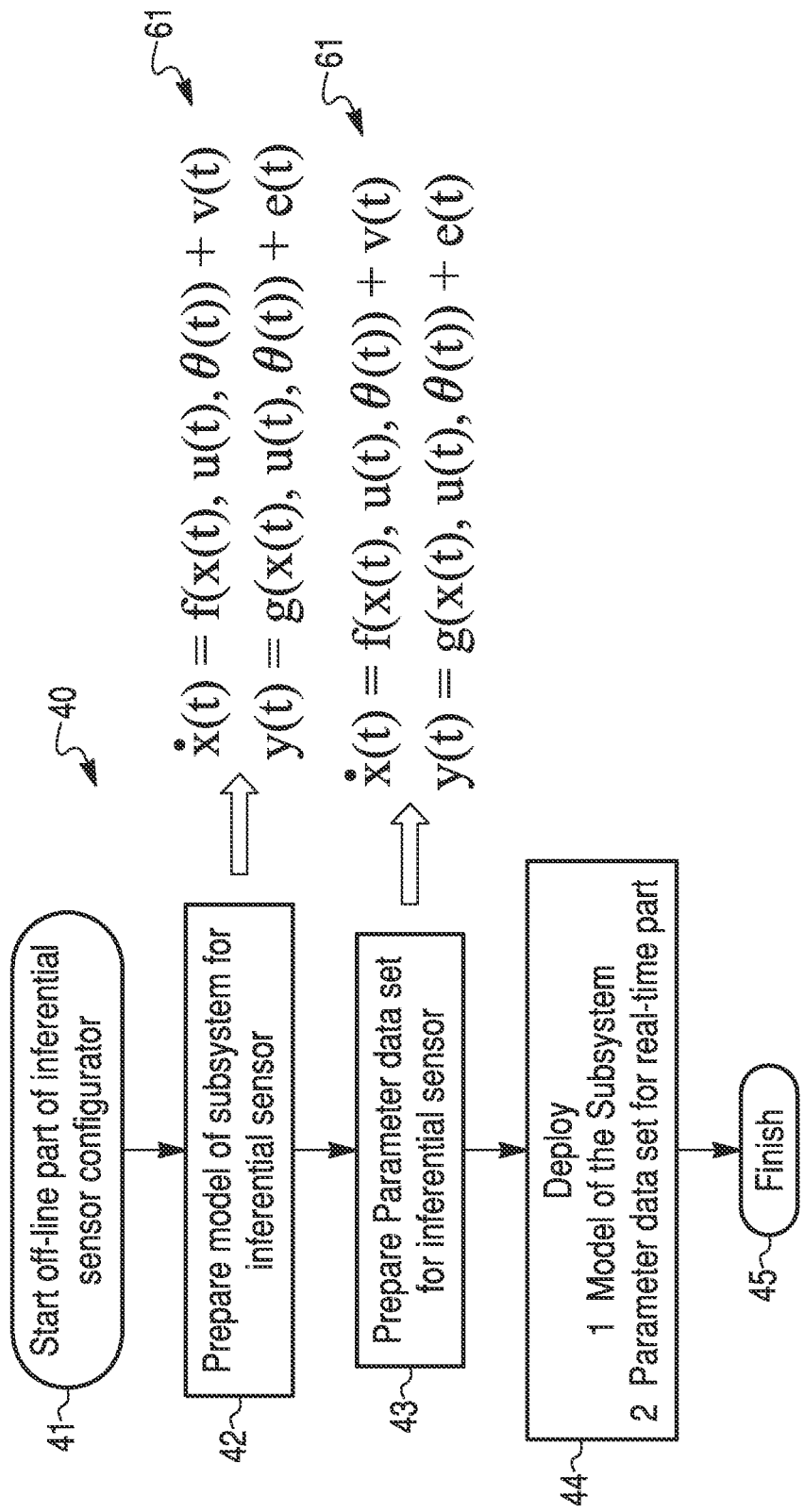
FIG. 10 is a diagram of a workflow for an off-line part of the inferential sensor.

An off-line part of the inferential sensor may involve a workflow as shown in a diagram 40 in FIG. 10. A start off-line part of an inferential sensor configuration may occur at a symbol 41. Preparing a model of a subsystem for the inferential sensor may occur at a symbol 42. At a symbol 43, there may be a preparing of a parameter data set for the inferential sensor. Symbols 42 and 43 may involve equations 61 in FIG. 3. For symbol 42, the emphasis of equations 61 may be on f and g. For symbol 43, the emphasis of equations 61 may be on θ(t), a parameter data set for the inferential sensor. A deployment at a symbol 44 may involve a model of the subsystem for the inferential sensor and a parameter data set for a real-time part. The workflow may end at a symbol 45. Calibration data set 51 may be regarded as an off-line part of the inferential sensor.

Figure 11:
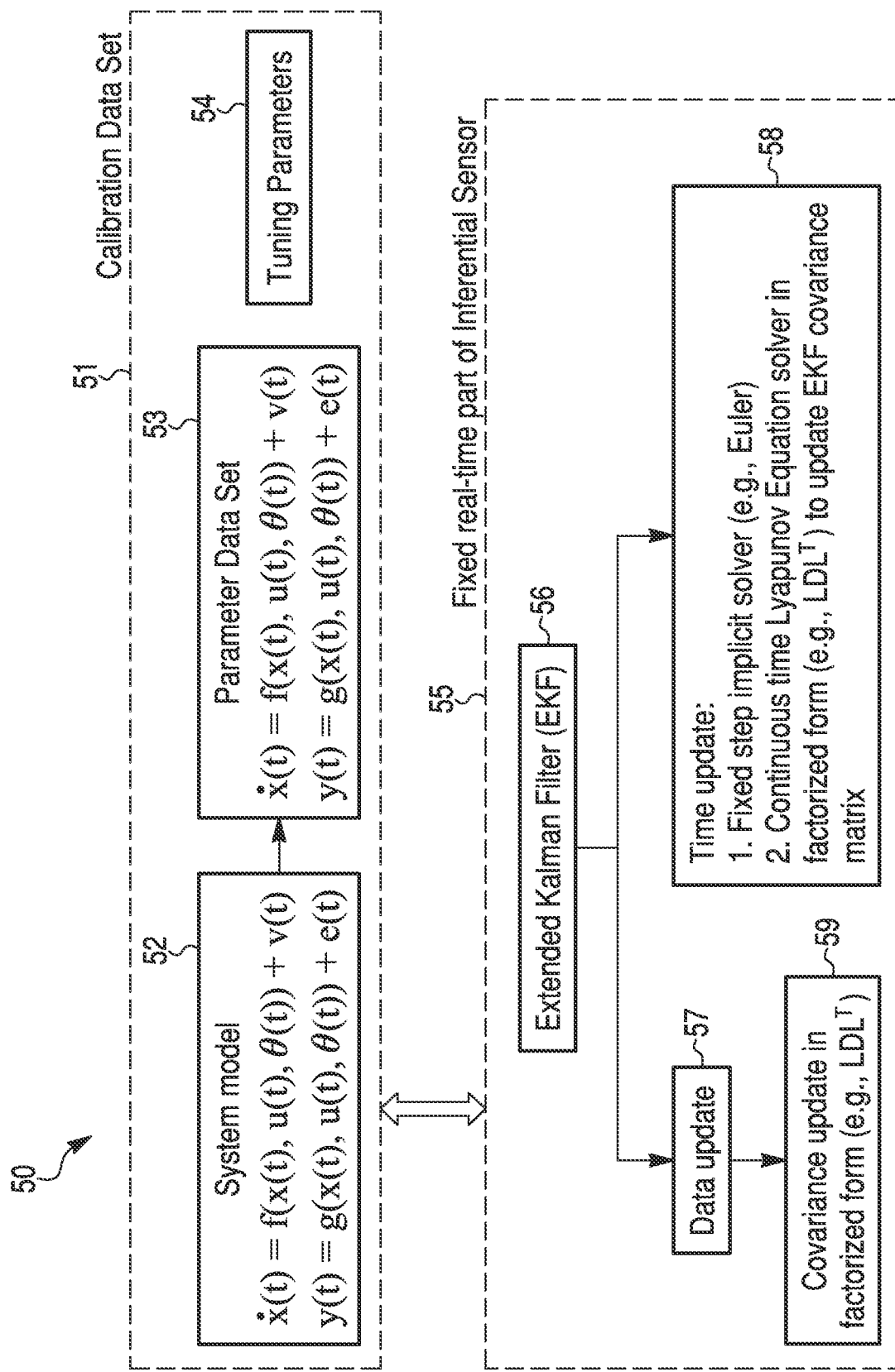
FIG. 11 is a diagram of a real-time template of the inferential sensor.

A real-time part of the inferential sensor may involve a template 50 in FIG. 11. A calibration data set 51 may incorporate a system model 52 involving equations 61 as shown in FIG. 3 with an emphasis on f and g. From model 52 may be a parameter data set 53 involving the same equations 61 with an emphasis on θ(t). Calibration data set 51 may also incorporate tuning parameters 54.

Calibration data set 51 may interact with a fixed real-time part 55 of the inferential sensor real-time template 50. Part 55 may incorporate an extended Kalman filter 56. From filter 56 may be a data update 57 and a time update 58. From data update 57 may be a covariance update 59 in factorized form (e.g., $LDL^T$). Time update 58 may involve a fixed step implicit solver (e.g., implicit Euler method). Also, time update 58 may involve a continuous Lyapunov equation solver in a factorized form (e.g., $LDL^T$) to update an extended Kalman filter covariance matrix. Fixed real-time part 55 may be regarded as an online part of the inferential sensor.

To recap, a system, for inferring quantities of an automotive subsystem, may incorporate an inferential sensor having one or more inputs that are provided to an automotive subsystem and one or more measured outputs provided by the subsystem, and having an output for providing one or more estimated quantities of the subsystem. A computer that processes the one or more inputs provided to the subsystem, and measured outputs from the subsystem, may provide the output of the inferential sensor for providing one or more estimated quantities of the subsystem. The inferential sensor may incorporate an off-line part and an on-line part. The off-line part may provide a model of the subsystem. The on-line part may provide the one or more estimated quantities of the subsystem.

The off-line part further may provide the model of the subsystem and a parameter data set for the on-line part. The on-line part may receive the one or more inputs provided to the subsystem and receive the measured outputs from the subsystem. The on-line part may further provide one or more confidence intervals of the estimated quantities of the subsystem.

The on-line part may incorporate a Kalman filter. The Kalman filter may be an extended Kalman filter that incorporates an implicit fixed step solver that updates the model of the subsystem, a covariance matrix of one or more estimated quantities and updates based on measured outputs from the subsystem. The subsystem may be an engine or an aftertreatment mechanism.

An inferential sensor may incorporate a computer, an off-line part and an on-line part. The off-line part may incorporate preparation of a model of a system that is a subject of an inferential sensor. The on-line part may incorporate an implicit fixed step solver to update the model of the system. The off-line part and the on-line part may be processed by the computer.

The off-line part may further incorporate a preparation of a parameter dataset for the model of the system that is the subject of the inferential sensor.

The on-line part may further incorporate a covariance matrix of an estimate of a state of the system. The covariance matrix of the estimate of the state of the system may be stored and updated based on measured data in a factorized form.

The parameter data set for the model of the system that is the subject of the inferential sensor may be stored in an automatically generated file.

The model of the system that is the subject of the inferential sensor may be described by a set of ordinary differential equations.

A time update of the covariance matrix of the estimate of the state of the system may be performed by an implicit fixed step solver utilizing a continuous Lyapunov equation.

If the model of the system that is a subject of the inferential sensor exists, then just a preparation of a parameter data set for the model of the system, that is the subject of the inferential sensor of the off-line part, may be needed for a new application of the inferential sensor to a system.

The inferential sensor may be utilized for obtaining an estimate for one or more items of a group consisting of ammonia storage in an selective catalytic reduction (SCR) catalyst, an SCR inlet NO/NO2 ratio, cross-sensitivity parameters of a NOX sensor, intake manifold/incylinder/exhaust manifold oxygen content or pressure, engine out NOx, and turbocharger speed, of an vehicle system.

The computer may be an engine control unit (ECU).

An approach for establishing an inferential sensor, may incorporate providing a computer, preparing a model for a subsystem being observed, populating a real-time template with data to be a calibration data set, and running periodically in real-time on the computer an inferential sensor with the model to obtain desired estimated variables.

The inferential sensor may provide estimates and confidence intervals of measurable physical quantities and/or non-measurable physical quantities in an aftertreatment system.

The inferential sensor may result in estimates and confidence intervals of readings of measurable physical quantities and/or non-measurable physical quantities of an engine. The estimates of readings of the measurable physical quantities from the inferential sensor may imply that one or more sensors of the directly measurable physical quantities can be eliminated.

The one or more sensors of the measurable physical quantities may be selected from a group consisting of an engine out NOx physical sensor, an intake manifold oxygen physical sensor, EGR mass flow physical sensor, fresh air mass flow physical sensor, turbocharger speed physical sensor, selective catalytic reduction (SCR) mid-brick NH3 physical sensor, and a tailpipe out NH3 physical sensor.

The approach may further incorporate configuring the inferential sensor to estimate one or more items from a group consisting of cross-sensitivity of NOx sensors to NH3, an SCR NH3 storage, and an SCR inlet NO/NO2 ratio.

In the present specification, some of the matter may be of a hypothetical or prophetic nature although stated in another manner or tense.

Although the present system and/or approach has been described with respect to at least one illustrative example, many variations and modifications will become apparent to those skilled in the art upon reading the specification. It is therefore the intention that the appended claims be interpreted as broadly as possible in view of the related art to include all such variations and modifications.

What is claimed is:

1. A system for inferring quantities of automotive subsystems, comprising:
a set of automotive subsystems configured to receive fuel and convert the fuel into exhaust, wherein the set of automotive subsystems includes a selective catalytic reduction (SCR) device configured to introduce ammonia that removes nitrogen oxides from the exhaust such that concentration limits of nitrogen oxides and ammonia in the exhaust are satisfied;
an engine control unit (ECU);
wherein the ECU includes an inferential sensor comprising an off-line part and an on-line part, wherein the off-line part of the inferential sensor is configured to:
prepare a model of the SCR device;
prepare a first parameter data set for the model, in response to preparing the model, to create a first real-time template for the SCR device;
receive an indication that the model is needed for a new application;
prepare a second parameter data set for the model, in response to receiving the indication that the model is needed for the new application, to create a second real-time template for the SCR device; and
wherein the on-line part of the inferential sensor is configured to:
receive one or more measured outputs provided by at least one of the automotive subsystems from the set of automotive subsystems;
identify an appropriate real-time template to use from at least the first and the second real-time templates based on the at least one of the automotive subsystems providing the one or more measured outputs;
populate the appropriate real-time template with the one or more measured outputs;
obtain a concentration of the nitrogen oxides in the exhaust from the populated real-time template;
calculate estimations for a set of cross-sensitivity parameters for a sensor based on the concentration of nitrogen oxides in the exhaust; and
calculate an estimation of ammonia storage in the SCR device based on the concentration of nitrogen oxides in the exhaust, wherein the estimation of ammonia storage provides the SCR device an amount of ammonia necessary to satisfy the concentration limits of nitrogen oxides and ammonia in the exhaust.

2. The system of claim 1, wherein:
the on-line part further provides one or more confidence intervals of the concentration of the nitrogen oxides.

3. The system of claim 2, wherein:
the on-line part comprises a Kalman filter;
the Kalman filter is an extended Kalman filter that comprises an implicit fixed step solver that updates the model of the at least one of the SCR device, a covariance matrix of the concentration of the nitrogen oxides and updates based on measured outputs from the SCR device.

4. An engine control unit (ECU) comprising:
a computer configured to generate concentration limits of nitrogen oxides and ammonia in an exhaust; and
an inferential sensor comprising:
an off-line part configured to:
prepare a model of an SCR device; and
prepare a first parameter data set for the model, in response to preparing the model, to create a real-time template for the SCR device;
receive an indication that the model is needed for a new application;
prepare a second parameter data set for the model, in response to receiving the indication that the model is needed for the new application, to create a second real-time template for the SCR device; and
an on-line part configured to:
receive calibration data provided by an automotive subsystem;
identify an appropriate real-time template to use from at least the first and the second real-time templates based on the automotive subsystem providing the calibration data;
populate the appropriate real-time template with the calibration data; and
obtain a concentration of the nitrogen oxides in the exhaust from the populated real-time template;
calculate estimations for a set of cross-sensitivity parameters for a sensor based on the concentration of nitrogen oxides in the exhaust; and
calculate an estimation of ammonia storage in the SCR device based on the concentration of nitrogen oxides in the exhaust, wherein the estimation of ammonia storage provides the SCR device an amount of ammonia necessary to satisfy the concentration limits of nitrogen oxides and ammonia in the exhaust generated by the computer.

5. The ECU of claim 4, wherein:
the parameter data set for the model of the SCR device is stored in an automatically generated file.

6. The ECU of claim 4, wherein:
the on-line part further comprises a covariance matrix of an estimate of a state of the SCR device;
the covariance matrix of the estimate of the state of the SCR device is stored and updated based on measured data in a factorized form; and
a time update of the covariance matrix of the estimate of the state of the SCR device is performed by an implicit fixed step solver utilizing a continuous Lyapunov equation.

7. The ECU of claim 4, wherein the model of the SCR device is described by a set of ordinary differential equations.

8. The ECU of claim 4, wherein the inferential sensor is utilized for obtaining additional estimates for one or more items of a group consisting of an SCR inlet NO/NO2 ratio, cross-sensitivity parameters of a NOX sensor, intake manifold/incylinder/exhaust manifold oxygen content or pressure, engine out NOx, and turbocharger speed, of an vehicle system.

9. The ECU of claim 4, wherein the computer is a rapid prototyping system.

10. A method of using an inferential sensor on an engine control unit (ECU) to monitor an automotive subsystem configured to receive fuel and convert the fuel into exhaust, comprising:
observing a selective catalytic reduction (SCR) device of the automotive subsystem using the ECU, wherein the SCR device is configured to introduce ammonia that removes nitrogen oxides from the exhaust such that concentration limits of nitrogen oxides and ammonia in the exhaust are satisfied;

automatically preparing a model for the SCR device using an off-line part of the inferential sensor;

automatically generating a first parameter data set for the model to create a first real-time template for the SCR device, and storing the first parameter data set on a computer using the off-line part of the inferential sensor;

receiving an indication that the model is needed for a new application;

preparing a second parameter data set for the model, in response to receiving the indication that the model is needed for the new application, to create a second real-time template for the SCR device using the off-line part of the inferential sensor;

receiving calibration data provided by the automotive subsystem using an on-line part of the inferential sensor;

identifying an appropriate real-time template to use from at least the first and the second real-time templates based on the automotive subsystems providing the calibration data using the on-line part of the inferential sensor;

populating the appropriate real-time template with the calibration data using the on-line part of the inferential sensor;

obtaining a concentration of nitrogen oxides in the exhaust from the populated real-time template using the on-line part of the inferential sensor;

calculating estimations for a set of cross-sensitivity parameters for a sensor based on the concentration of nitrogen oxides in the exhaust; and calculating an estimation of ammonia storage in the SCR device based on the concentration of nitrogen oxides in the exhaust, wherein the estimation of ammonia storage provides the SCR device an amount of ammonia necessary to satisfy the concentration limits of nitrogen oxides and ammonia in the exhaust.

11. The method of claim 10, wherein the inferential sensor provides confidence intervals of the concentration of the nitrogen oxides.

12. The method of claim 10, wherein the on-line part comprises a Kalman filter and the Kalman filter is an extended Kalman filter that comprises an implicit fixed step solver that updates the model of the at least one of the SCR device, a covariance matrix of the concentration of the nitrogen oxides, and updates based on measured outputs from the SCR device.

13. The method of claim 12, wherein the calibration data for the real-time template of the SCR device is stored in an automatically generated file.

14. The method of claim 13, further comprising configuring the inferential sensor to estimate one or more items from a group consisting of cross-sensitivity of NOx sensors to NH3, an SCR NH3 storage, and a selective catalytic reduction (SCR) inlet NO/NO2 ratio.

15. The system of claim 1, wherein:

the off-line part includes 1) the real-time template of the SCR device, which is developed independent of observation of the automotive subsystem for which the inferential sensor may be configured for an application, and 2) the calibration data for use with the real-time template to calibrate the inferential sensor for the application, the calibration data is generated from a model of the automotive subsystem; and the on-line part estimates one or more quantities for the application of the inferential sensor associated with the automotive subsystem in real time during operation of the automotive subsystem.

* * * * *